United States Patent [19]

Fung et al.

[11] Patent Number: 5,116,982
[45] Date of Patent: May 26, 1992

[54] PREPARATION OF FLUOROHALOPHENOLS AND N-ACYFLUOROHALOANILINES

[75] Inventors: Alexander P. Fung, Martinez; M. Moklesur Rahman, Antioch; Thomas J. Dietsche, Berkeley, all of Calif.

[73] Assignee: DowElanco, Indianapolis, Ind.

[21] Appl. No.: 562,782

[22] Filed: Aug. 6, 1990

[51] Int. Cl.$^5$ .............................................. C07F 5/02
[52] U.S. Cl. .................................. 546/13; 546/2; 546/3; 546/8; 546/9; 546/22; 558/411; 564/161; 564/162; 568/774; 568/775
[58] Field of Search ............... 546/9, 13, 22, 8, 3, 546/2; 568/774, 775; 558/411; 564/161, 162

[56] References Cited

FOREIGN PATENT DOCUMENTS

0204535A1 12/1986 European Pat. Off. .

OTHER PUBLICATIONS

T. Umemoto et al., Bull. Chem. Soc. Japan, 59, 3625–3629 (1986).

J. March, Advanced Organic Chemistry, 3rd Ed., 510–511, (1985).

T. Umemoto et al., Tetrahedron Letters, vol. 27, 3271–3274, 4465–4468 (1986).

T. Umemoto et al., J. Organic Chemistry, 54, 1726–1731 (1989).

Taub, Chemistry and Industry, 1962, pp. 558–559.

Primary Examiner—Glennon H. Hollrah
Assistant Examiner—S. Kumar
Attorney, Agent, or Firm—D. Wendell Osborne

[57] ABSTRACT

Chloro and bromophenols and N-acylanilines are fluorinated in an ortho or para position with an N-fluoropyridinium salt to obtain fluorohalophenols and N-acylfluorohaloanilines, which can be further converted to fluorophenols and N-acylfluoroanilines by reduction. Thus, o-fluorophenol is obtained by fluorination of p-bromophenol with 2-chloro-6-(trichloromethyl)-pyridinium fluoroborate and reduction of the product obtained with sodium formate and a palladium catalyst. N-fluoropyridinium salts having trichloromethyl substituents are disclosed.

18 Claims, No Drawings

PREPARATION OF FLUOROHALOPHENOLS AND N-ACYFLUOROHALOANILINES BACKGROUND OF THE INVENTION

The present invention relates to a process for preparing phenols and N-acylanilines substituted with fluorine in the 2-, 4- or 6-position and to N-fluoro-pyridinium salt fluorinating agents useful in the process.

Halophenols and N-acylhaloanilines substituted in the 2-, 4-, or 6-position and with fluorine and with one or more bromine or chlorine are valuable intermediates in the preparation of herbicides, insecticides, fungicides, and pharmaceuticals. Many such compounds are known and processes for their preparation involving diazotization chemistry and halogen exchange with potassium or cesium fluoride chemistry have been reported. Such processes are difficult to carry out and often produce large amounts of waste. Because the subject compounds have been accessible only through relatively complex, multistep processes, their utility as intermediates has been confined to situations where the final product commands a very high price. It would be of considerable interest to discover a simple process for the preparation of fluorohalophenols and fluorohaloacylanilides which has the potential of providing such compounds to industry at a cost that would make them suitable as intermediates for products with other applications. Similarly, it would be of considerable interest to discover fluorinating agents useful in such processes.

It has recently been reported (European application 204535, published Dec. 10, 1986) that phenol, 4-t-butyl-phenol, and 4-(methoxycarbonylmethyl)-phenol and acetanilide react with certain N-fluoro-pyridinium salts to produce derivatives fluorinated in the 2-position and, in the cases of phenol and acetanilide, the 4-position. The fluorination of chloro and fluoro substituted compounds, however, typically involves replacement of the halogen by fluorine as a major reaction.

SUMMARY OF THE INVENTION

It has now been found that phenols and N-acyl-anilines substituted with fluorine in the 2-, 4-, or 6-position and with at least one bromine or chlorine can be prepared conveniently and simply by fluorination with an N-fluoropyridinium compound. Good yields are obtained.

The invention includes a process for the preparation of a fluorohalophenol or N-acylfluoro-haloaniline product of the formula (Formula 1)

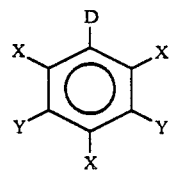

Formula I wherin
each X and each Y independently represents H, F, Cl, Br, $C_1$–$C_4$ alkyl, $C_1$–$C_4$ alkoxy, $CF_3$, CN, $CO_2H$, or $CO_2$($C_1$–$C_4$ alkyl) with the proviso that at least one X represents F, at least one X or one Y represents Cl or Br and at least one X or one Y represents H: and D represents OH or $NHCO(C_1$–$C_4$ alkyl) which comprises contacting a halophenol or N-acylhaloaniline of the formula (Formula 11)

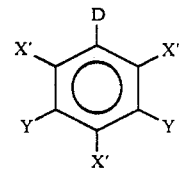

Formula II wherein
each X' independently represents H, F, Cl, Br, $C_1$–$C_4$ alkyl, $C_1$–$C_4$ alkoxy, $CF_3$, CN, $CO_2H$, or $CO_2$($C_1$–$C_4$ alkyl) with the proviso that one X' represents H, at least one Y or one additional X' represents H, and at least one X' or one Y represents Cl or Br: and D represents OH or $NHCO(C_1$–$C_4$ alkyl) with an N-fluoropyridinium salt fluorinating agent of the formula (Formula III)

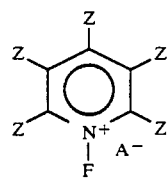

Formula III wherein
each Z independently represents H, Cl, F, $C_1$–$C_4$ alkyl, $C_1$–$C_4$ alkoxy, CN, $CO_2(C_1$–$C_4$ alkyl), $CF_3$, or $CCl_3$ with the proviso that not more than two of Z represent CN, $CO_2(C_1$–$C_4$ alkyl), $CF_3$, or $CCL_3$; and A— represents $(C_1$–$C_4)R_fSO_3$—, $FSO_3$—, $SbF_6$—, $BF_4$—, $PF_6$—, $TaF_6$—, or $NbF_6$—
under conditions conducive to fluorination.

$R_f$ as used herein represents a perfluoroalkyl moiety that may be linear or branched.

The preparation of fluorohalophenols employing the process is often preferred and the preparation of 2-fluoro-4-chlorophenol and 2-fluoro-4-bromophenol by the reaction of 4-chlorophenol and 4-bromophenol, respectively, with an N-fluoropyridinium salt are important embodiments of the invention.

N-Fluoropyridinium salts derived from 2-chloro-6-(trichloromethyl) pyridine are often especially advantageous in the process. N-Fluoropyridinium salts derived from pyridine are also often especially preferred.

The fluorohalophenols and N-acylfluorohalo-anilines prepared in the process of the present invention are useful intermediates in the preparation of valuable insecticides, herbicides, fungicides, and pharmaceuticals.

The invention includes a process for preparing fluorophenols and N-acylfluoroanilines of Formula I

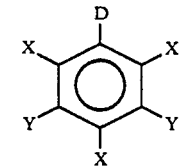

Formula I wherein
each X and each Y independently represents H,

F, $C_1$-$C_4$ alkyl, $C_1$-$C_4$ alkoxy, $CF_3$, CN, $CO_2H$, or $CO_2(C_1$-$C_4$ alkyl) with the proviso that at least one X represents F and at least two of X and Y represent H; and D represents OH or $NHCO(C_1$-$C_4$ alkyl) which comprises preparing a fluorohalophenol or N-acylfluorohaloaniline compound of Formula I wherein each X and each Y independently represents H, F, Cl, Br, $C_1$-$C_4$ alkyl, $C_1$-$C_4$ alkoxy, $CF_3$, CN, $CO_2H$, or $CO_2(C_1$-$C_4$ alkyl) with the proviso that at least one X represents F, at least one X or one Y represents Cl or Br and at least one X or one Y represents H; and D represents OH or $NHCO(C_1$-$C_4$ alkyl) by the process described herein and subsequently removing the bromo or chloro substituents by reduction using known methods.

The invention further includes N-fluoropyridinium salt compounds of Formula III

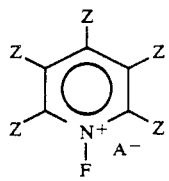

Formula III wherein

Z represents H, Cl, or $CCL_3$ with the proviso that no more than 4 of Z represent H and 1 or 2 of Z represent $CCL_3$; and A− represents $(C_1$-$C_4)RfSO_3-$, $FSO_3-$, $SbF_6-$, $BF_4-$, $PF_6-$, $TaF_6-$, or $NbF_6-$.

N-fluoropyridinium salts having tetrafluoroborate anions are often preferred as are salts having N-fluoro-2-chloro-6-(trichloromethyl)pyridinium cations.

DETAILED DESCRIPTION OF THE INVENTION

The fluorohalophenols and N-acylfluorohalo-anilines prepared by the process of the present invention are characterized by having a fluoro substituent in an ortho or para position and at least one chloro or bromo substituent. These compounds include the phenols of Formula I (D represents OH) wherein each X and each Y independently represents H, F, Cl, Br, $C_1$-$C_4$ alkyl, $C_1$-$C_4$ alkoxy, $CF_3$, CN, $CO_2H$, or $CO_2(C_4$ alkyl) with the proviso that at least one X represents F, at least one X or one Y represents Cl or Br and at least one X or one Y represents H and the N-acylanilines of Formula I (D represents $NHCO(C_1$-$C_4$ alkyl) wherein X and Y are defined in the same way.

Typical examples of fluorohalophenols that can be prepared by the process include 2-fluoro-4-bromophenol, 2-fluoro-4-chlorophenol, 2-fluoro-3-bromophenol, 2-fluoro-5-chlorophenol, 2-fluoro-4,6-dichlorophenol, 2-fluoro-4-bromo-6-methylphenol, 2-fluoro-5-chloro-4-butoxyphenol, 2-fluoro-4-(trifluoromethyl)-6-chloro-phenol, 2,6-difluoro-4-bromophenol, 3-fluoro-5-bromo-salicylic acid, methyl 5-fluoro-3-chlorosalicylate, 4-fluoro-2,6-dichlorophenol, 4-fluoro-2-bromo-6-methylphenol, 2-fluoro-6-bromo-4-cyanophenol, and 2,4-difluoro-6-chloro-5-(trifluoromethyl)phenol.

Typical examples of N-acylfluorohaloanilines that can be prepared by the process include N-acetyl-2-fluoro-4-bromoaniline, N-acetyl-2-fluoro-4-chloro-aniline, N-butanoyl-2-fluoro-5-bromo-4-methylaniline, N-propanoyl-2-fluoro-5-chloroaniline, N-acetyl-2-fluoro-4,6-dichloroaniline, N-acetyl-2-fluoro-4-bromo-6-chloroaniline, N-(1 TM methylethanoyl)-2-fluoro-5-chloro-4-(1,1-dimethylethyl)aniline, N-acetyl-2-fluoro-6-(tri-fluoromethyl)-4-bromoaniline, N-acetyl-2,6-difluoro-4-bromoaniline, N-acetyl-3-fluoro-5-bromoanthranilic acid acid, methyl N-acetyl-5-fluoro-3-chloroanthranilate, N-acetyl-4-fluoro-2,6-dichloroaniline, N-acetyl-4-fluoro-2-chloro-6-ethylaniline and N-acetyl-2,4-di-fluoro-5-chloro-6-(trifluoromethyl)aniline.

The starting material halophenols and N-acyl-anilines of the present invention are characterized by having at least one chloro or bromo substituent. These compounds include the phenols of Formula II (D represents OH) wherein each X' and each Y independently represents H, F, Cl, Br, $C_1$-$C_4$ alkyl, $C_1$-$C_4$ alkoxy, $CF_3$, CN, $CO_2H$, or $CO_2(C_1$-$C_4$ alkyl) with the proviso that at least one X' represents F, at least one X' or one Y represents Cl or Br and at least one X' or one Y represents H and the N-aoylanilines of Formula II (D represents $NHCO(C_1$-$C_4$ alkyl) wherein X' and Y are defined in the same way. Typical examples of appropriate starting materials include 4-chlorophenol, 4-bromophenol, N-acetyl-4-bromo-2-(trifluoromethyl)-aniline, and other phenols and N-acylanilines that are analogous to the product compounds named above except that they lack of one or more fluorine atoms. It is preferred to employ starting phenols and anilines wherein the possibility of forming isomers by reaction at non-identical, alternate 2-, 4-, and 6-positions does not exist. Thus, for example, symmetrical phenols and anilines wherein one or two of the ortho and para positions (X' substituents) are other than hydrogen are often preferred.

Suitable starting material N-fluoropyridinium salts are those given by Formula III wherein each Z independently represents H, Cl, F, $C_1$-$C_4$ alkyl, $C_1$-$C_4$ alkoxy, CN, $CO_2(C_1$-$C_4$ alkyl), $CF_3$, or $CCL_3$ with the proviso that no more than two of Z represent CN, $CO_2(C_1$-$C_4$ alkyl), $CF_3$ or $CCL_3$ and A- represents an anion that stabilizes the N-fluoropyridinium cation, such as $(C_1$-$C_4)RfSO_3-$, $FSO_3-$, $SbF_6-$, $BF_4-$, $PF_6-$, $TaF_6-$, or $NbF_6-$.

It is often preferred to employ an N-fluoropyridinium salt derived from unsubstituted pyridine. Those derived from picolines and lutidines are also sometimes preferred. In other operations, N-fluoropyridinium salts derived from chloropyridines, such as 2,6-dichloropyridine, 3,5-dichloropyridine, 2,3,5,6-tetrachloropyridine, and the like or from chloro(trichloromethyl)pyridines, such as 2-chloro-6-(trichloromethyl)pyridine are preferred. Preferred anions (A−) include $BF_4-$, and $CF_3SO_3-$.

Many N-fluoropyridinium salt reagents are known in the art, for example, in European Patent Application 204,535, published Dec. 10, 1986 and Tetrahedron Letters. 27. 3271-3274 (1986). Those compounds of Formula III wherein one or two of the Z substituents are $CCL_3$, however, are novel. The present invention relates to these novel fluorinating agents as compounds. N-fluoropyridinium salts derived from 2-chloro-6-(trichloromethyl)pyridine are of special interest.

The N-fluoropyridinium salts of Formula III having one or two trichloromethyl groups as substituents are generally prepared by adding fluorine gas diluted with helium or nitrogen to a solution of an appropriately substituted pyridine compound and a perfluorometalloid compound, such as boron trifluoride or tantalum pentafluoride, or an alkali metal salt of a very strong acid, such as trifluoromethanesulfonic acid or fluorosulfonic acid, in an inert solvent, such as acetonitrile. The reaction is typically carried out with cooling to temperatures below about 10° C. and with good mixing. An amount of fluorine and of perfluorometalloid compound or alkali metal salt of a very strong acid in excess of the theoretically required amount based on the amount of pyridine compound present is often advantageously employed. The desired salt forms quiokly and can be recovered or used essentially immediately. The N-fluoropyridinium salts prepared are generally solids that can be recovered by adding a non-solvent, such as ethyl ether or pentane, and collecting the solids that form by filtration or centrifugation. Alternately, the solids can be recovered by evaporation of the solvent under reduced pressure or the mixture obtained can be used as a fluorinating agent without isolation of the N-fluoropyridinium salt.

The process of the present invention is generally carried out in a solvent. Suitable solvents are those that do not react with N-fluoropyridinium salts under the reaction conditions, in which the starting materials are at least somewhat soluble, and which boil at about 40° C. or higher. Acetonitrile, methylene chloride, chloroform, carbon tetrachloride, 1,2-dichloroethane, 1,1,2-trichloroethane, 1,1,1-tri-choloroethane, 1,1,2-trichloroethylene, 1,1,2,2-tetra-chloroethane, perchloroethylene, tetrahydrofuran, dioxane, dimethoxyethane, chlorobenzene, and 1,2-dichlorobenzene are examples of suitable solvents. 1,1,2-Trichloroethane is sometimes preferred. Mixtures of solvents can also be employed. A solvent may not be necessary if the mixture of starting materials is a liquid and the N-methylpyridinium salt has some solubility in the compound being fluorinated, but it is generally preferred to employ one.

The process is conducted under conditions conducive to fluorination. Temperatures of about 30 to about 120° C. are typically employed. Temperatures above about 40° C. are generally preferred as are temperatures below 100° C. The process proceeds well at any pressure compatible with the solvent and temperature employed. It is generally preferred to conduct the process at atmospheric pressure or under the back-pressure typically found in industrial reactors. The reaction is usually carried out in the absence of more than adventitious water and means are sometimes employed to exclude water from the system. The process is sometimes carried out under a blanket of an inert gas, such as nitrogen or argon so as to exclude oxygen. Agitation is usually employed to ensure continuously complete mixing.

The reactants can be mixed in any order. They are typically combined and the mixture then heated to the desired reaction temperature with agitation. The reaction consumes equal molar quantities of the reactants when monofluorination is desired and two moles of N-fluoropyridinium salt to one of halophenol or N-acylhaloaniline when difluorination is desired. Approximately the theoretically consumed ratios of the starting materials for the desired reaction are generally employed, but a substantial excess of one or the other can be used with success. It is often advantageous to use an excess of the N-fluoropyridinium salt.

The reaction is continued until a significant amount of the desired product is formed. The exact time will depend on the starting materials, the solvent, and the temperature and other operational variables. Generally, reaction times of about 1 to about 30 hours are suitable.

The fluorohalophenols and N-acylfluorohalo-anilines prepared in the process of the present invention can be recovered by conventional means. For example, any solvents can be removed by evaporation under reduced pressure and the residue fractionally distilled under reduced pressure or, if it is a solid, recrystallized from a solvent.

The desired products can generally be obtained in yields of about 40 percent or more. The yield can be optimized for each specifically desired product by selection of the best N-fluoropyridinium salt fluorinating agent, the best solvent, and the best temperature. The required selection can readily be made using the procedures and teachings of the present specifioation and claims in conjunction with those of the identified prior art.

The products of the present process, compounds of Formula 11, are useful intermediates that can be employed directly to produce a wide variety of end use products.

The products of Formula I wherein each X and each Y independently represents H, F, Cl, Br, $C_1-C_4$ alkyl, $C_1-C_4$ alkoxy, $CF_3$, CN, $CO_2H$, or $CO_2(C_1-C_4$ alkyl) with the proviso that at least one X represents F, at least one X or one Y represents Cl or Br and at least one X or one Y represents H; and D represents OH or $NHCO(C_1-C_4$ alkyl) can be used in the preparation of compounds of Formula I wherein each X and each Y independently represents H, F, $C_1-C_4$ alkyl, $C_1-C_4$ alkoxy, $CF_3$, CN, $CO_2H$, or $CO_2(C_1-C_4$ alkyl) with the proviso that at least one X represents F and at least two of X or one Y represent H; and D represents OH or $NHCO(C_1-C_4$ alkyl); that is, phenols and N-acylanilines possessing at least one fluorine substituent in a 2-, 4-, or 6-position, no bromine or chlorine substituents, and not more than three total substituents. The transformation can be carried out by known reduction methods typically employed to selectively reduce chloro or bromo substituents to hydrogen in the presence of fluoro substituents. Several appropriate methods are summarized in March's *Advanced Organic Chemistry*, 3rd ed., pages 510–511. For example, the reduction can be accomplished with sodium formate using a palladium on carbon catalyst. This reduction is generally carried out in an alcoholic solvent, such as 2-propanol, at a temperature between about 30 and about 100° C. It is generally complete within a few hours.

Examples of fluorophenols and fluoroanilines that can be prepared in the above manner include 2-fluorophenol, 2-fluoro-4-cyanophenol, 3-fluorosalicylic acid, 4-fluoro-2-methylphenol, 2,6-difluorophenol, N-acetyl-2,6-difluoroaniline, N-acetyl-2-fluoroaniline, N-acetyl-2-fluoro-6-(trifluoro-methyl) aniline, and N-propionyl-3-fluoroanthranilic acid.

The following examples are presented to illustrate the invention. They should not be construed as limiting its scope.

EXAMPLES

Example 1. Preparation of N-Fluoro-2,6-dichloropyridinium Trifluoromethanesulfonate.

A 100 ml (milliliters) 3-necked round bottom flask was equipped with a magnetic stirring bar, a fluorine-helium inlet tube, and a gas outlet tube connected to a granular alumina trap and then to a 5 percent aqueous caustic trap. A 1.0 g (gram) (6.8 mmol (millimole))

sample of 2,6-dichloropyridine, 1.03 g (6.0 mmol) of sodium trifluoromethanesulfonate, and 40 ml of anhydrous acetonitrile were added and the mixture cooled to $-40°$ C. A 1:9 mixture of fluorine and helium then was passed into the mixture with stirring at the rate of 30 ml per minute until 15 mmol of fluorine had been added. The fluorine gas mixture was replaced with nitrogen gas and the mixture was allowed to warm to ambient temperature. The mixture was filtered and the filtrate was concentrated by evaporation under reduced pressure to obtain 0.75 g (40 percent of theory) of the title compound as a yellowish solid. The compound had $19_F$ NMR absorptions ($CD_3CN$, $CFCl_3$ standard) at 31.6 ppm (s) N-F and $-78$ ppm (s) $CF_3$ in a 1:3 ratio as required by the structure.

Example 2. Preparation of N-Fluoro-2-chloro-6-(tri-chloromethyl)pyridinium Tetrafluoroborate.

A 250 ml 3-necked round bottom flask was equipped with a magnetic stirring bar, a fluorine-helium inlet tube, and a gas outlet tube connected to a granular alumina trap and then to a 5 percent aqueous caustic trap. A 5.0 g (21.8 mmol) sample of 2-chloro-6-(trichloromethyl)pyridine, 3.0 ml of boron trifluoride etherate, and 40 ml of anhydrous acetonitrile were added and the mixture cooled to 3 to 5° C. A 1:9 mixture of fluorine and helium then was passed into the mixture with stirring at the rate of 50 ml per minute until 33 mmol of fluorine had been added. The fluorine gas mixture was replaced with nitrogen gas and the mixture was allowed to warm to ambient temperature. Diethyl ether (80 ml) was added and the solid that formed was collected by filtration. The 4.37 g of off-white solid obtained was recrystallized from ethyl acetate to obtain 4.25 g (60 percent of theory) of the title compound as a white solid melting at 170-172° C. The compound had $19_F$ NMR absorptions ($CD_3CN$, $CFCl_3$ standard) at 29.5 ppm (s) N-F and $-150.8$ ppm (s) $BF_4$ in a 1:4 ratio as required by the structure.

The following compounds were prepared in the same manner and obtained as white solids:

N-Fluoro-2-chloro-4-(trichloromethyl)pyridinium tetrafluoroborate; m.p., 167-169° C., $19_F$ NMR absorptions ($CD_3CN$) at 39.9 ppm (s) N-F and $-150.9$ ppm (s) $BF_4$ (62 percent yield);

N-Fluoro-2,3-dichloro-6-(trichloromethyl)-pyridinium tetrafluoroborate; m.p., 171-172° C., $19_F$ NMR absorptions ($CD_3CN$) at 40.0 ppm (s) N-F and $-150.3$ ppm (s) $BF_4$ (42 percent yield):

N-Fluoro-2-chloro-5-(trichloromethyl)pyridinium tetrafluoroborate; $19_F$ NMR absorptions ($CD_3CN$) at 41.9 ppm (s) N-F and $-150.9$ ppm (s) $BF_4$ and $^1H$ NMR absorptions at 10.04 ppm (d,d), 9.12 ppm (d,d), and 8.53 ppm (m) (82 percent yield);

N-Fluoro-2,3,4-trichloro-6-(trichloromethyl)-pyridinium tetrafluoroborate: $19_F$ NMR absorptions ($CD_3CN$) at 37.6 ppm (s) N-F and -150.1 ppm (s) $BF_4$ and a $^1H$ NMR absorption at 8.01 ppm (d) (55 percent yield);

N-Fluoro-2,6-dichloro-4-(trichloromethyl)pyridinium tetrafluoroborate: $19_F$ NMR absorptions ($CD_3CN$) at 35.0 ppm (s) N-F and -150.3 ppm (s) $BF_4$ and a $^1H$ NMR absorption at 8.85 ppm (d) (63 percent yield); and N-Fluoro-2,3,5,6-tetrachloropyridinium tetrafluoroborate; (43 percent yield).

Example 3. Preparation of 2-Fluoro-4-chlorophenol.

a) A mixture of 1.29 g (10.0 mmol) of 4-chlorophenol, 2.47 g (10.0 mmol) of N-fluoropyridinium triflate, and 50 ml of 1,1,2-trichloroethane was placed in a 100 ml 3-necked round bottomed flask equipped with a magnetic stirring bar, a thermometer, and a reflux condenser. The mixture was heated to 45° C. and allowed to react at that temperature for 23 hours. The mixture was then allowed to cool and the volatiles were removed by evaporation under reduced pressure. Analysis of the residue by standardized gas-liquid chromatography using a mass spectrometer detector and by $19_F$ and $^1H$ NMR indicated that the title product was present in 42 percent conversion.

b) The procedure of a) was used except that 3.21 g (10.0 mmol) of N-fluoro-2,3,5,6-tetrachloro-pyridinium fluoroborate was employed as the fluorinating agent. There was a slight exotherm on mixing. The mixture was heated to 45° C. and allowed to react at that temperature for 3 hours. The mixture was then allowed to cool and the volatiles were removed by evaporation under reduced pressure. Analysis of the residue by standardized gas-liquid chromatography using a mass spectrometer detector indicated that the title product was present in 81 percent conversion.

c) The procedure of a) was used except that 3.33 g of N-fluoro-2-chloro-6-(trichloromethyl)-pyridinium fluoroborate was employed as the fluorinating agent. There was a slight exotherm on mixing. The mixture was heated to 45° C. and allowed to react at that temperature for 3 hours. The mixture was then allowed to cool and the volatiles were removed by evaporation under reduced pressure. The residue was distilled and the fraction boiling at 96-98° C. under 40 mm (millimeters) Hg (5.3 kPa (kiloPascals)) pressure was collected to obtain 1.0 g (68 percent of theory) of the title compound. The product identity was confirmed by its known $19_F$ and $^1H$ NMR spectra.

d) The procedure of a) was used except that 0.64 g of 4-chlorophenol was employed, the fluorinating agent was 1.89 g of N-fluoro-2,3-dichloro-6-(trichloromethyl)pyridinium fluoroborate, and 40 ml of solvent was employed. There was a slight exotherm on mixing. The mixture was heated to 45° C. and allowed to react at that temperature for 3 hours. The mixture was then allowed to cool and the volatiles were removed by evaporation under reduced pressure. Analysis of the residue by standardized gas-liquid chromatography using a mass spectrometer detector indicated that the title product was present in 69 percent yield.

Example 4. Preparation of 2-Fluoro-4-bromophenol.

A mixture of 0.86 g of 4-bromophenol, 1.67 g of N-fluoro-2-chloro-6-(trichloromethyl)pyridinium fluoroborate, and 40 ml of 1,1,2-trichloroethane was placed in a 100 ml 3-necked round bottomed flask equipped with a magnetic stirring bar, a thermometer, and a reflux condenser. The mixture was heated to 45° C. and allowed to react at that temperature for 23 hours under nitrogen. The mixture was then allowed to cool. Analysis by standardized gas-liquid chromatography using a mass spectrometer detector indicated that the title product was present in 74 percent conversion. The product identity was confirmed by its known $19_F$ and $^1H$ NMR spectra.

The above procedure was repeated with a variety of N-fluoropyridinum salts and the results are shown in the following table:

| N-Fluoropyridinium Salt | Conditions | Conversion (percent) |
|---|---|---|
| N-Fluoropyridinium Triflate | 100° C./28 hr | 44 |
| N-Fluoro-2,6-dichloro-pyridinium Tetrafluoroborate | 100° C./5 hr | 53 |
| N-Fluoro-2,6-dichloro-pyridinium Tetrafluoroborate | 70° C./10 hr | 86 |
| N-Fluoro-2,3,4,5-tetra-chloropyridinium Tetrafluoroborate | 45° C./9 hr | 77 |
| N-Fluoro-2,3,5,6-tetra-chloropyridinium Tetrafluoroborate | 45° C./6 hr | 87 |
| N-Fluoro-2,3-dichloro-6-(trichloromethyl)pyridinium Tetrafluoroborate | 45° C./23 hr | 80 |
| N-Fluoro-2,3-dichloro-5-(trichloromethyl)pyridinium Tetrafluoroborate | 45° C./23 hr | 51 |
| N-Fluoro-2,6-dichloro-4-(trichloromethyl)pyridinium Tetrafluoroborate | 45° C./23 hr | 71 |
| N-Fluoro-2-chloro-6-(trichloromethyl)pyridinium Tetrafluoroborate | 45° C./23 hr | 74 |
| N-Fluoro-2-chloro-5-(trichloromethyl)pyridinium Tetrafluoroborate | 45° C./23 hr | 76 |
| N-Fluoro-2-chloro-4-(trichloromethyl)pyridinium Tetrafluoroborate | 45° C./23 hr | 67 |

Example 5. Preparation of 4-Fluoro-2,6-dichlorophenol

A mixture of 0.82 g of 2,6-dichlorophenol, 1.67 g of N-fluoro-2-chloro-6-(trichloromethyl) pyridinium rfluoroborate, and 40 ml of 1,1,2-trichloroethane was placed in a 100 ml 3-necked round bottomed flask equipped with a magnetic stirring bar, a thermometer, and a reflux condenser. The mixture was heated to 55° C. and allowed to react at that temperature for 8 hours under nitrogen. The mixture was then allowed to cool. Analysis by standardized gas-liquid chromatography using a mass spectrometer detector indicated that the title product was present in 24 percent conversion. The product identity was confirmed by its known $19_F$ and $^1H$ NMR spectra.

Example 6. Preparation of N-Acetyl-2-fluoro-4-bromoaniline

A mixture of 1.17 g (5.0 mmol) of N-acetyl-4-bromoaniline, 1.20 g (5.0 mmol) of N-fluoropyridinium triflate, and 50 ml of 1,1,2-trichloroethane was placed in a 100 ml 3-necked round bottomed flask equipped with a magnetic stirring bar, a thermometer, and a reflux condenser. The mixture was heated to 100° C. and allowed to react at that temperature for 20 hours. The mixture was then allowed to cool and the volatiles were removed by evaporation under reduced pressure. Analysis of the residue by standardized gas-liquid chromatography using a mass spectrometer detector indicated that the title product was present in 28 percent yield and that the balance of the N-acetyl-4-bromoaniline was still present as unreacted material.

Example 7. Preparation of 2-Fluorophenol a) A mixture of 0.74 g (5.0 mmol) of 2-fluoro-4-chlorophenol, 0.68 g (10.0 mmol) of sodium formate, 0.2 g of 1.0 percent palladium on carbon catalyst, and 30 ml of 2-propanol was placed in a 100 ml 3-necked round bottomed flask equipped with a magnetic stirring bar, a thermometer, and a reflux condenser. The mixture was heated to 65° C. and allowed to react at that temperature for 3 hours. It was then allowed to cool, was filtered, and the filtrate was concentrated by evaporation under reduced pressure. Analysis of the residue by standardized gas-liquid chromatography using a mass spectrometer detector and by $19_F$ and $^1H$ NMR spectroscopy indicated that this was the title compound and that it was obtained in 95 percent yield.

b) The procedure of a) was followed except that 2.96 g of 2-fluoro-4-chlorophenol, 2.72 g of sodium formate, 0.2 g of catalyst, and 40 ml of 2-propanol were employed. The mixture was heated to 65° C. and allowed to react at that temperature for 3 hours. It was then allowed to cool, was filtered, and the filtrate was concentrated by evaporation under reduced pressure. Analysis of the residue by standardized gas-liquid chromatography using a mass spectrometer detector indicated that it was 98 percent the title compound. The residue was flash distilled to obtain 1.84 g (81 percent of theory) of the title compound boiling at 90–92° C. under 70 mm Hg (9.3 kPa) pressure.

What is claimed is:

1. A process for the preparation of a fluorohalophenol or N-acylfluorohaloaniline product of the formula

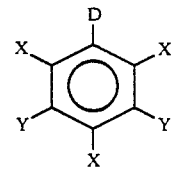

wherein
each X and each Y independently represents H, F, Cl, Br, $C_1$–$C_4$ alkyl, $C_1$–$C_4$ alkoxy, $CF_3$, CN, $CO_2H$, or $CO_2$($C_1$–$C_4$ alkyl) with the proviso that at least one X represents F, at least one X or one Y represents Cl or Br, and at least one X or one Y represents H: and D represents OH or $NHCO$($C_1$–$C_4$ alkyl) which comprises contacting a halophenol or N-acylhaloaniline starting compound of the formula

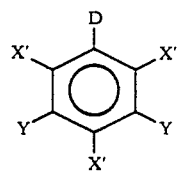

wherein
each X' independently represents H, F, Cl, Br, $C_1$–$C_4$ alkyl, $C_1$–$C_4$ alkoxy, $CF_3$, CN, $CO_2H$, or $CO_2$(-$C_1$–$C_4$ alkyl) with the proviso that one X' represents H, at least one Y or one additional X' represents H, and at least one X' or one Y represents Cl or Br: and D represents OH or $NHCO$($C_1$–$C_4$ alkyl) with an N-fluoropyridinium salt fluorinating agent of the formula

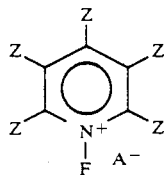

wherein
each Z independently represents H, Cl, F, $C_1$-$C_4$ alkyl, $C_1$-$C_4$ alkoxy, CN, $CO_2(C_1$-$C_4$ alkyl), or $CCl_3$ with the proviso that not more than two of Z represent CN, $CO_2(C_1$-$C_4$ alkyl), or $CCL_3$; and
A- represents $(C_1$-$C_4)RfSO_3-$, $FSO_3-$, $SbF_6-$, $BF_4-$, $PF_6-$, $TaF_6-$, or $NbF_6-$
under conditions conducive to fluorination.

2. A process according to claim 1 wherein D represents OH.

3. A process according to claim 1 wherein D represents $NHCO(C_1$-$C_4$ alkyl).

4. A process according to claim 1 wherein the anion A- of the fluorinating agent is $BF_4-$.

5. A process according to claim 1 wherein each Z represents H, Cl, or $CCL_3$, with the proviso that not more than 2 of Z represent $CCL_3$.

6. A process according to claim 1 wherein the temperature is maintained at between about 30° C. and about 120° C.

7. A process according to claim 2 wherein the halophenol starting compound is 4-chlorophenol or 4-bromophenol and the product is 2-fluoro-4-chlorophenol or 2-fluoro-4-bromophenol.

8. A process according to claim 3 wherein the starting compound is an N-acyl-4-chloroaniline or an N-acyl-4-bromoaniline.

9. A process according to claim 3 wherein acyl is acetyl.

10. A process for the preparation of a fluorophenol or N-acylfluoroaniline compound of the formula

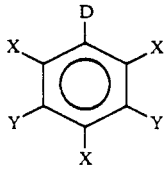

wherein
each X independently represents H, F, $C_1$-$C_4$ alkyl, $C_1$-$C_4$ alkoxy, $CF_3$, CN, $CO_2H$, or $CO_2(C_1$-$C_4$ alkyl) with the proviso that at least one X represents F and at least two of Y and X represent H; and
D represents OH or $NHCO(C_1$-$C_4$ alkyl) which comprises
a) preparing a fluorohalophenol or N-acylfluorohaloaniline product of the formula

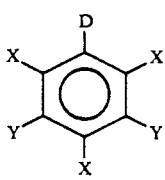

wherein
each X and each Y independently represents H, F, Cl, Br, $C_1$-$C_4$ alkyl, $C_1$-$C_4$ alkoxy, $CF_3$, CN, $CO_2H$, or $CO_2(C_1$-$C_4$ alkyl) with the proviso that at least one X represents F, at least one X or one Y represents Cl or Br, and at least one X or one Y represents H; and D represents OH or $NHCO(C_1$-$C_4$ alkyl) by contacting a halophenol or N-acylhaloaniline starting compound of the formula

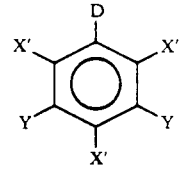

wherein
each X' independently represents H, F, Cl, Br, $C_1$-$C_4$ alkyl, $C_1$-$C_4$ alkoxy, $CF_3$, CN, $CO_2H$, or $CO_2(C_1$-$C_4$ alkyl) with the proviso that one X' represents H, at least one Y or one additional X' represents H, and at least one X' or one Y represents Cl or Br; and
D represents OH or $NHCO(C_1$-$C_4$ alkyl) with an N-fluoropyridinium salt fluorinating agent of the formula

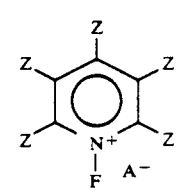

wherein
each Z independently represents H, Cl, F, $C_1$-$C_4$ alkyl, $C_1$-$C_4$ alkoxy, CN, $CO_2(C_1$-$C_4$ alkyl), or $CCL_3$ with the proviso that no more than two of Z represent CN, $CO_2(C_1$-$C_4$ alkyl), or $CCL_3$; and
A- represents $(C_1$-$C_4)RfSO_3-$, $FSO_3-$, $SbF_6-$, $BF_4-$, $PF_6-$, $TaF_6-$, or $NbF_6-$
under conditions conducive to fluorination; and
b) subsequently removing all of the chloro and bromo substituents by reduction using known methods.

11. A process according to claim 10 wherein D represents OH.

12. A process according to claim 10 wherein D represents $NHCO(C_1$-$C_4$ alkyl).

13. A process according to claim 10 wherein the anion A- of the fluorinating agent is $BF_4-$.

14. A process according to claim 10 wherein each Z represents H, Cl, or $CCL_3$, with the proviso that not more than 2 of Z represent $CCL_3$.

15. A process according to claim 10 wherein the temperature is maintained at between about 30° C. and about 120° C.

16. A process according to claim 11 wherein the halophenol starting compound is 4-chlorophenol or 4-bromophenol and the compound obtained is 2-fluorophenol.

17. A process according to claim 12 wherein the starting compound is an N-acyl-4-chloroaniline or an N-acyl-4-bromoaniline and an N-acyl-2,6-difluoroaniline compound or an an N-acyl-2- fluoroaniline compound is obtained.

18. A process according to claim 17 wherein acyl is acetyl.

* * * * *